(12) United States Patent
Suresh et al.

(10) Patent No.: US 12,336,773 B2
(45) Date of Patent: Jun. 24, 2025

(54) INTERACTION BETWEEN USER-INTERFACE AND MASTER CONTROLLER

(71) Applicant: Intuitive Surgical Operations, Inc., Sunnyvale, CA (US)

(72) Inventors: Ashwinram Suresh, San Jose, CA (US); Joey Chau, Cupertino, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 784 days.

(21) Appl. No.: 17/016,340

(22) Filed: Sep. 9, 2020

(65) Prior Publication Data
US 2021/0030491 A1   Feb. 4, 2021

Related U.S. Application Data

(63) Continuation of application No. 15/526,698, filed as application No. PCT/US2015/060330 on Nov. 12, 2015, now Pat. No. 10,786,315.
(Continued)

(51) Int. Cl.
*A61B 34/00* (2016.01)
*A61B 17/00* (2006.01)
(Continued)

(52) U.S. Cl.
CPC .............. *A61B 34/25* (2016.02); *A61B 34/30* (2016.02); *A61B 34/35* (2016.02); *A61B 34/37* (2016.02);
(Continued)

(58) Field of Classification Search
CPC ..... G06F 3/04812; A61B 34/25; A61B 34/30; A61B 34/35; A61B 34/37; A61B 34/70;
(Continued)

(56) References Cited

U.S. PATENT DOCUMENTS

| 4,942,538 A | 7/1990 | Yuan et al. |
| 5,625,576 A | 4/1997 | Massie et al. |

(Continued)

FOREIGN PATENT DOCUMENTS

| CN | 118370610 | 7/2024 |
| WO | WO-2007030173 A1 | 3/2007 |

(Continued)

OTHER PUBLICATIONS

Vogel eat al., "Distant Freehand Pointing and Clicking on Very Large, High Resolution Displays", UIST'05, Oct. 23-27, 2005, pp. 33-42. (Year: 2005).*
(Continued)

*Primary Examiner* — Hwei-Min Lu
(74) *Attorney, Agent, or Firm* — Schwegman, Lundberg & Woessner, P.A.

(57) ABSTRACT

A system to control the interaction between a user-interface of a teleoperated surgical system and an input device of the teleoperated surgical system, the system comprising a first master controller communicatively coupled to the teleoperated surgical system, a feedback control communicatively coupled to the first master controller, and a display device communicatively coupled to the teleoperated surgical system and configured to display the user interface. The feedback control is configured to restrict the movement of the first master controller based on a state of the user interface changing from a previous state.

22 Claims, 13 Drawing Sheets

Related U.S. Application Data

(60) Provisional application No. 62/079,402, filed on Nov. 13, 2014.

(51) Int. Cl.
  *A61B 34/30* (2016.01)
  *A61B 34/35* (2016.01)
  *A61B 34/37* (2016.01)
  *A61B 90/00* (2016.01)
  *G06F 3/04812* (2022.01)

(52) U.S. Cl.
  CPC ............ *A61B 34/74* (2016.02); *A61B 34/76* (2016.02); *A61B 90/37* (2016.02); *G06F 3/04812* (2013.01); *A61B 2017/00203* (2013.01); *A61B 2017/00207* (2013.01); *A61B 2017/00216* (2013.01); *A61B 2034/741* (2016.02); *A61B 2034/742* (2016.02); *A61B 2034/743* (2016.02); *A61B 2034/744* (2016.02); *A61B 90/03* (2016.02); *A61B 2090/365* (2016.02)

(58) Field of Classification Search
  CPC ......... A61B 34/74; A61B 34/76; A61B 90/37; A61B 90/03; A61B 2034/741; A61B 2034/742; A61B 2034/743; A61B 2034/744; A61B 2090/365; A61B 2017/00203; A61B 2017/00207; A61B 2017/00216
  USPC .......................................... 700/257; 715/856
  See application file for complete search history.

(56) References Cited

U.S. PATENT DOCUMENTS

| | | | |
|---|---|---|---|
| 5,749,362 A | 5/1998 | Funda et al. | |
| 5,786,805 A * | 7/1998 | Barry ................. | G06F 3/04812 345/159 |
| 5,788,688 A | 8/1998 | Bauer et al. | |
| 5,799,055 A | 8/1998 | Peshkin et al. | |
| 6,392,675 B1 * | 5/2002 | Becker ................ | G06F 3/04812 715/858 |
| 6,424,885 B1 | 7/2002 | Niemeyer et al. | |
| 6,493,608 B1 | 12/2002 | Niemeyer et al. | |
| 6,522,906 B1 | 2/2003 | Salisbury, Jr. et al. | |
| 6,659,926 B2 | 12/2003 | Haag | |
| 6,659,939 B2 | 12/2003 | Moll et al. | |
| 6,671,581 B2 | 12/2003 | Niemeyer et al. | |
| 6,714,201 B1 | 3/2004 | Grinstein et al. | |
| 6,714,939 B2 | 3/2004 | Saldanha et al. | |
| 6,799,065 B1 | 9/2004 | Niemeyer | |
| 7,131,073 B2 | 10/2006 | Rosenberg et al. | |
| 7,206,626 B2 | 4/2007 | Quaid, III | |
| 7,206,627 B2 | 4/2007 | Abovitz et al. | |
| 7,234,937 B2 | 6/2007 | Sachdeva et al. | |
| 8,095,200 B2 | 1/2012 | Quaid, III | |
| 8,359,114 B2 | 1/2013 | Steingart et al. | |
| 8,398,541 B2 | 3/2013 | Dimaio et al. | |
| 8,551,084 B2 | 10/2013 | Hauck et al. | |
| 8,571,628 B2 | 10/2013 | Kang et al. | |
| 8,657,736 B2 | 2/2014 | Diolaiti et al. | |
| 8,696,548 B2 | 4/2014 | Gilboa | |
| 9,266,239 B2 | 2/2016 | Miller | |
| 10,123,846 B2 | 11/2018 | Suresh et al. | |
| 10,786,315 B2 | 9/2020 | Suresh et al. | |
| 11,135,029 B2 | 10/2021 | Suresh et al. | |
| 11,723,734 B2 | 8/2023 | Suresh | |
| 2002/0033799 A1 * | 3/2002 | Mallett ................... | G06F 3/038 345/156 |
| 2003/0030621 A1 * | 2/2003 | Rosenberg ............ | G09B 23/28 345/156 |
| 2003/0220541 A1 * | 11/2003 | Salisbury, Jr. ......... | A61B 1/313 600/101 |
| 2004/0091845 A1 | 5/2004 | Azerad et al. | |
| 2005/0027397 A1 * | 2/2005 | Niemeyer .............. | A61B 34/37 700/245 |
| 2005/0093847 A1 | 5/2005 | Altkorn et al. | |
| 2006/0058616 A1 | 3/2006 | Marquart et al. | |
| 2008/0033240 A1 * | 2/2008 | Hoffman ............... | G06F 3/0346 600/109 |
| 2008/0168364 A1 * | 7/2008 | Miller ..................... | G06F 3/033 715/762 |
| 2009/0012533 A1 | 1/2009 | Barbagli et al. | |
| 2010/0073150 A1 | 3/2010 | Olson et al. | |
| 2010/0177042 A1 * | 7/2010 | Chen ..................... | G06F 3/03547 345/159 |
| 2010/0191100 A1 | 7/2010 | Anderson et al. | |
| 2010/0234857 A1 | 9/2010 | Itkowitz et al. | |
| 2010/0309122 A1 * | 12/2010 | Abe ...................... | G06F 3/04812 345/157 |
| 2010/0311028 A1 | 12/2010 | Bell, III et al. | |
| 2011/0015569 A1 | 1/2011 | Kirschenman et al. | |
| 2011/0050566 A1 * | 3/2011 | Sawai ..................... | G06F 3/041 345/157 |
| 2011/0066406 A1 | 3/2011 | Tsai et al. | |
| 2011/0082587 A1 | 4/2011 | Ziaei et al. | |
| 2011/0238010 A1 | 9/2011 | Kirschenman et al. | |
| 2012/0001644 A1 | 1/2012 | Baarman et al. | |
| 2012/0004894 A1 | 1/2012 | Butler et al. | |
| 2012/0056840 A1 * | 3/2012 | Benko ................... | G06F 3/04812 345/173 |
| 2012/0109152 A1 * | 5/2012 | Quaid, III ............. | A61B 34/74 606/130 |
| 2012/0278711 A1 | 11/2012 | Altkorn et al. | |
| 2013/0023899 A1 | 1/2013 | Green | |
| 2013/0111322 A1 * | 5/2013 | Marum .................. | G06F 40/174 715/223 |
| 2013/0245375 A1 | 9/2013 | Dimaio et al. | |
| 2014/0081455 A1 | 3/2014 | Goldberg et al. | |
| 2014/0088941 A1 | 3/2014 | Banerjee et al. | |
| 2014/0187857 A1 | 7/2014 | Wilson et al. | |
| 2014/0276938 A1 | 9/2014 | Hsu et al. | |
| 2015/0153833 A1 * | 6/2015 | Pinault .................. | G06F 3/011 345/156 |
| 2015/0286295 A1 * | 10/2015 | Pepe ...................... | G06F 3/0362 345/163 |
| 2016/0229052 A1 * | 8/2016 | Touma .................. | B25J 9/1658 |
| 2017/0333139 A1 | 11/2017 | Suresh et al. | |
| 2019/0099230 A1 | 4/2019 | Suresh et al. | |

FOREIGN PATENT DOCUMENTS

| | | | |
|---|---|---|---|
| WO | WO-2010104753 A1 | 9/2010 | |
| WO | WO-2010147766 A1 | 12/2010 | |
| WO | WO-2015167531 A2 * | 11/2015 | ......... G06F 3/04812 |
| WO | WO-2016077543 A1 | 5/2016 | |
| WO | WO-2016077552 A1 | 5/2016 | |

OTHER PUBLICATIONS

Notice of Allowance mailed Jun. 3, 2021 for U.S. Appl. No. 16/153,405, filed May 10, 2018, 8 pages.
Non Final Office Action mailed Dec. 18, 2020 for U.S. Appl. No. 16/153,405, filed Oct. 5, 2018, 7 pages.
Claims filed dated Oct. 8, 2019 for U.S. Appl. No. 16/153,405, filed Oct. 5, 2018, 5 pages.
Extended European Search Report for Application No. EP15858228. 8, mailed on Jul. 11, 2018, 9 pages.
Final Office Action mailed Dec. 10, 2019 for U.S. Appl. No. 16/153,405, filed Oct. 5, 2018.
International Preliminary Report on Patentability for Application No. PCT/US2015/060317, mailed on May 26, 2017, 8 pages.
International Preliminary Report on Patentability for Application No. PCT/US2015/060330, mailed on May 26, 2017, 12 pages.
International Search Report and Written Opinion for Application No. PCT/US2015/060317, mailed on Jan. 27, 2016, 12 pages.
International Search Report and Written Opinion for Application No. PCT/US2015/060330, mailed on Feb. 1, 2016, 14 pages.

(56) References Cited

OTHER PUBLICATIONS

Non Final Office Action mailed Apr. 4, 2019 for U.S. Appl. No. 15/526,698, filed May 12, 2017, 20 pages.
Non Final Office Action mailed Feb. 6, 2018 for U.S. Appl. No. 15/526,696, filed May 12, 2017, 8 pages.
Non Final Office Action mailed Jul. 8, 2019 for U.S. Appl. No. 16/153,405, filed Oct. 5, 2018, 9 pages.
Non Final Office Action mailed Feb. 18, 2020 for U.S. Appl. No. 15/526,698, filed May 12, 2017, 7 pages.
Non Final Office Action mailed Feb. 21, 2019 for U.S. Appl. No. 16/153,405, filed Oct. 5, 2018, 5 pages,.
Notice of Allowance mailed Oct. 16, 2019 for U.S. Appl. No. 15/526,698, filed May 12, 2017, 11 pages.
Notice of Allowance mailed Dec. 19, 2019 for U.S. Appl. No. 15/526,698, filed May 12, 2017, 2 pages.
Notice of Allowance mailed Jun. 22, 2018 for U.S. Appl. No. 15/526,696, filed May 12, 2017, 7 pages.
Notice of Allowance mailed Jan. 27, 2020 for U.S. Appl. No. 15/526,698, filed May 12, 2017, 5 pages.
Preliminary Amendment mailed Dec. 21, 2018 for U.S. Appl. No. 16/153,405, filed Oct. 5, 2018, 12 pages.
Response filed May 7, 2018 to Non Final Office Action mailed Feb. 6, 2018 for U.S. Appl. No. 15/526,696, filed May 12, 2017, 18 pages.
Response filed Oct. 8, 2019 to Non Final Office Action mailed Jul. 8, 2019 for U.S. Appl. No. 16/153,405, filed Oct. 5, 2018, 12 pages.
Response filed Jul. 11, 2019 to Non Final Office Action mailed Apr. 4, 2019 for U.S. Appl. No. 15/526,698, filed May 12, 2017, 9 pages.
Response filed Apr. 29, 2019 to Non Final Office Action mailed Feb. 21, 2019 for U.S. Appl. No. 16/153,405, filed Oct. 5, 2018, 9 pages.
Vertut, Jean and Phillipe Coiffet, Robot Technology: Teleoperation and Robotics Evolution and Development, English translation, Prentice-Hall, Inc., Inglewood Cliffs, NJ. USA 1986, vol. 3A, 332 pages.
Extended European Search Report for Application No. EP21160293.3 mailed on Jul. 21, 2021, 10 pages.
Final Office Action mailed Sep. 15, 2020 for U.S. Appl. No. 16/153,405, filed Oct. 5, 2018.
Non Final Office Action mailed Mar. 10, 2020 for U.S. Appl. No. 16/153,405, filed Oct. 5, 2018, 7 pages.
Notice of Allowance mailed Jul. 22, 2020 for U.S. Appl. No. 15/526,698, filed May 12, 2017, 5 pages.
Response filed Feb. 17, 2020 to Final Office Action mailed Dec. 10, 2019 for U.S. Appl. No. 16/153,405, filed Oct. 5, 2018, 12 pages.
Response filed May 18, 2020 to Non Final Office Action mailed Feb. 18, 2020 for U.S. Appl. No. 15/526,698, filed May 12, 2017, 9 pages.
Response filed Jul. 23, 2020 to Non Final Office Action mailed Mar. 10, 2020 for U.S. Appl. No. 16/153,405, filed Oct. 5, 2018, 10 pages.
"European Application Serial No. 21160293.3, Communication Pursuant to Article 94(3) EPC mailed Jun. 25, 2024", 8 pages.
"European Application Serial No. [Pending], Communication Pursuant to Article 94(3) EPC mailed Jun. 25, 2024", 8 pages.
"Chinese Application Serial No. 201580069917.X, Response filed Aug. 23, 2024 to Notice of Reexamination mailed Jul. 14, 2023", with English claims, 21 pages.
"Korean Application Serial No. 10-2022-7044344, Response filed Aug. 30, 2024 to Final Office Action mailed May 31, 2024", with English claims, 11 pages.
"European Application Serial No. 21160293.3, Response filed Oct. 31, 2024 to Communication Pursuant to Article 94(3) EPC mailed Jun. 25, 2024", with English claims, 11 pages.

* cited by examiner

INTERACTION BETWEEN USER-INTERFACE AND MASTER CONTROLLER

RELATED APPLICATIONS

This application is a continuation of and claims the benefit of priority under 35 U.S.C. § 120 to U.S. patent application Ser. No. 15/526,698, filed on May 12, 2017, which is a U.S. National Stage Filing under 35 U.S.C. 371 from International Application No. PCT/US2015/060330, Nov. 12, 2015, and published as WO 2016/077552 A1 on May 19, 2016, which claims the benefit of priority under 35 U.S.C. § 119(e) to U.S. Provisional Patent Application No. 62/079,402, filed on Nov. 13, 2014, each of which is incorporated by reference herein in its entirety.

FIELD

Embodiments described herein generally relate to training and in particular, to systems and methods for controlling a user-interface.

BACKGROUND

Minimally invasive medical techniques are intended to reduce the amount of tissue that is damaged during diagnostic or surgical procedures, thereby reducing patient recovery time, discomfort, and deleterious side effects. Teleoperated surgical systems that use robotic technology (so-called surgical robotic systems) may be used to overcome limitations of manual laparoscopic and open surgery. Advances in telepresence systems provide surgeons views inside a patient's body, an increased number of degrees of motion of surgical instruments, and the ability for surgical collaboration over long distances.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in the figures of the accompanying drawings in which.

DESCRIPTION OF EMBODIMENTS

The following description is presented to enable any person skilled in the art to create and use systems and methods of a medical device simulator. Various modifications to the embodiments will be readily apparent to those skilled in the art, and the generic principles defined herein may be applied to other embodiments and applications without departing from the spirit and scope of the inventive subject matter. Moreover, in the following description, numerous details are set forth for the purpose of explanation. However, one of ordinary skill in the art will realize that the inventive subject matter might be practiced without the use of these specific details. In other instances, well known machine components, processes and data structures are shown in block diagram form in order not to obscure the disclosure with unnecessary detail. Flow diagrams in drawings referenced below are used to represent processes. A computer system may be configured to perform some of these processes. Modules within flow diagrams representing computer-implemented processes represent the configuration of a computer system according to computer program code to perform the acts described with reference to these modules. Thus, the inventive subject matter is not intended to be limited to the embodiments shown, but is to be accorded the widest scope consistent with the principles and features disclosed herein.

Teleoperated Surgical System

Figure 1:
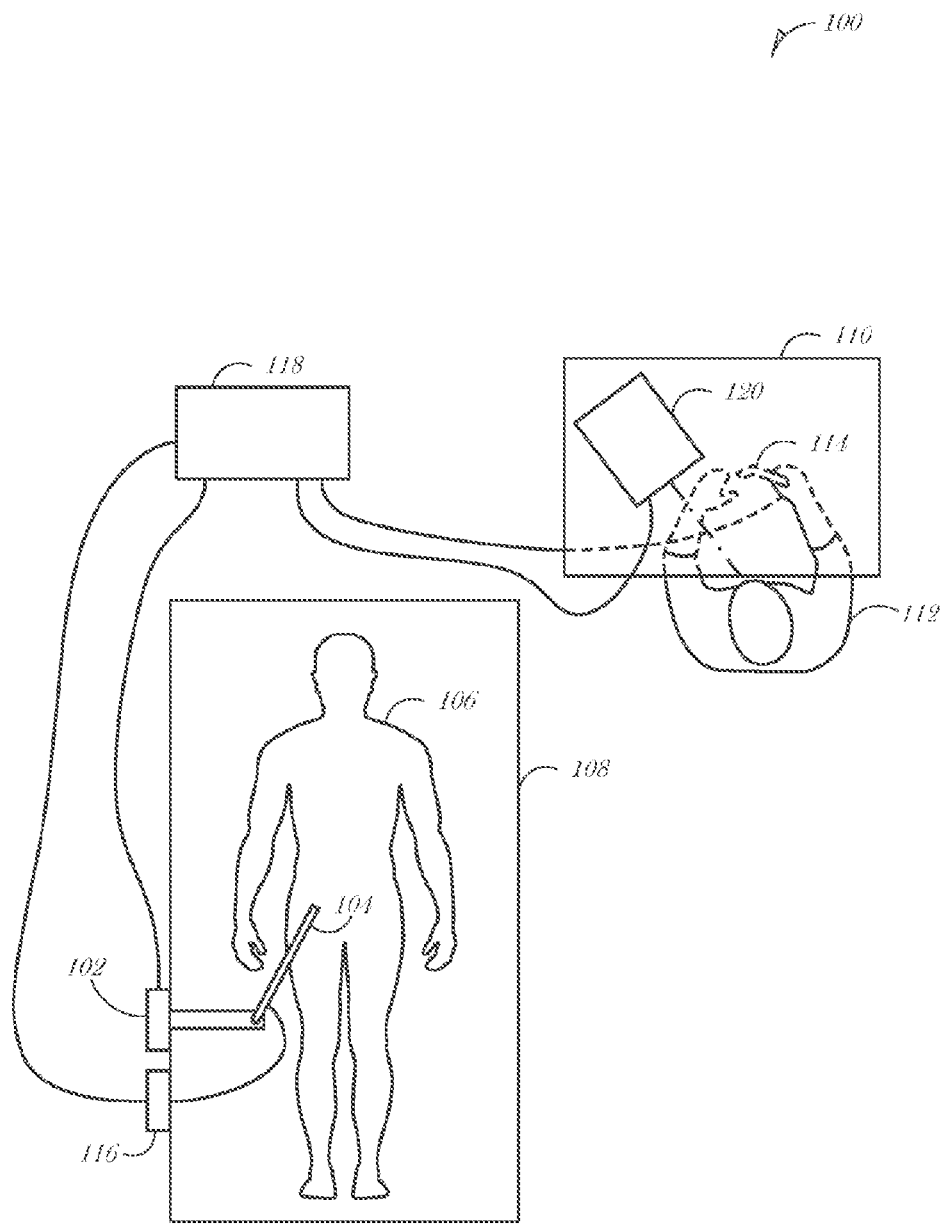
FIG. 1 is a schematic drawing illustrating a teleoperated surgical system, according to an embodiment.

FIG. 1 is a schematic drawing illustrating a teleoperated surgical system 100, according to an embodiment. The teleoperated surgical system 100 includes a surgical manipulator assembly 102 for controlling operation of a surgical instrument 104 in performing various procedures on a patient 106. The assembly 102 is mounted to or located near an operating table 108. A master assembly 110 allows a surgeon 112 to view the surgical she and to control the manipulator assembly 102.

In alternative embodiments, the teleoperated surgical system 100 may include more than one manipulator assembly 102. The exact number of manipulator assemblies will depend on the surgical procedure and the space constraints within the operating room, among other factors.

The master assembly 110 may be located in the same room as the operating table 108. However, it should be understood that the surgeon 112 may be located in a different room or a completely different building from the patient 106. The master assembly 110 generally includes one or more control device(s) 114 for controlling the manipulator assembly 102. The control device(s) 114 may include any number of a variety of input devices, such as gravity-balanced arms, joysticks, trackballs, gloves, trigger-grips, hand-operated controllers, hand motion sensors, voice recognition devices, eye motion sensors, or the like. In some embodiments, the control device(s) 114 may be provided with the same degrees of freedom as the associated surgical instruments 104 to provide the surgeon 112 with telepresence, or the perception that the control device(s) 114 are integral with the instrument 104 so that the surgeon 112 has a strong sense of directly controlling the instrument 104. In some embodiments, the control device 114 is a manual input device that moves with six degrees of freedom or more, and which may also include an actuatable handle or other control feature (e.g., one or more buttons, switches, etc.) for actuating instruments (for example, for closing grasping jaws, applying an electrical potential to an electrode, delivering a medicinal treatment, or the like).

A visualization system 116 provides a concurrent two- or three-dimensional video image of a surgical site to the surgeon 112 as the surgeon 112 operates one or more instruments. The visualization system 116 may include a viewing scope assembly such that visual images may be captured by an endoscope positioned within the surgical site. The visualization system 116 may be implemented as hardware, firmware, software or a combination thereof which interact with or are otherwise executed by one or more computer processors, which may include the processors of a control system 118.

A display system 120 may display a visual image of the surgical site and surgical instruments 104 captured by the visualization system 116. The display system 120 and the control devices 114 may be oriented such that the relative positions of the visual imaging device in the scope assembly and the surgical instruments 104 are similar to the relative positions of the surgeon's eyes and hands so the operator (e.g., surgeon 112) may manipulate the surgical instrument 104 with the control devices 114 as if viewing a working volume adjacent to the instrument 104 in substantially true presence. By "true presence" it is meant that the presentation of an image is a true perspective image simulating the viewpoint of an operator that is physically manipulating the surgical instruments 104.

The control system 118 includes at least one processor (not shown) and typically a plurality of processors for effecting control between the surgical manipulator assembly 102, the master assembly 110, and the display system 116. The control system 118 also includes software programming instructions to implement some or all of the methods described herein. While the control system 118 is shown as a single block in the simplified schematic of FIG. 1, the control system 118 may comprise a number of data processing circuits (e.g., on the surgical manipulator assembly 102 and/or on the master assembly 110). Any of a wide variety of centralized or distributed data processing architectures may be employed. Similarly, the programming code may be implemented as a number of separate programs or subroutines, or may be integrated into a number of other aspects of the teleoperated systems described herein. In various embodiments, the control system 118 may support wireless communication protocols such as Bluetooth®, IrDA, HomeRF, IEEE 802.11, DECT, and Wireless Telemetry.

In some embodiments, the control system 118 may include servo controllers to provide force and torque feedback from the surgical instrument 104 to the control devices 114. Any suitable conventional or specialized servo controller may be used. A servo controller may be separate from, or integral with, the manipulator assembly 102. In some embodiments, the servo controller and the manipulator assembly 102 are provided as part of a robotic arm cart positioned adjacent to the patient 106. The servo controllers transmit signals instructing the manipulator assembly 102 to move the instrument 104, which extends into an internal surgical site within the patient body via openings in the body.

For the purposes of this document, the control devices 114 may be referred as a "master controller" and the surgical instrument 104 may be referred to as a "slave."

Each manipulator assembly 102 supports at least one surgical instrument 104 (e.g., "slave") and may comprise a series of non-teleoperated, manually articulatable linkages and a teleoperated robotic manipulator. The linkages may be referred to as a set-up structure, which includes one or more links coupled with joints that allows the set-up structure to be positioned and held at a position and orientation in space. The manipulator assembly 102 may be driven by a series of actuators (e.g., motors). These motors actively move the teleoperated robotic manipulators in response to commands from the control system 118. The motors are further coupled to the surgical instrument 104 so as to advance the surgical instrument 104 into a naturally or surgically created anatomical orifice and move the surgical instrument 104 and manipulator assembly 102 in multiple degrees of freedom that may include three degrees of linear motion (e.g., x, y, and z linear motion) and three degrees of rotational motion (e.g., roll, pitch, yaw). Additionally, the motors may be used to actuate an effector of the surgical instrument 104 such as an articulatable effector for grasping tissues in the jaws of a biopsy device or an effector for obtaining a tissue sample or for dispensing medicine, or another effector for providing other treatment as described more fully below, for example. U.S. Pat. No. 6,671,581 (Niemeyer et al.), which is incorporated by reference, contains further information on camera referenced control in a minimally invasive surgical apparatus.

In an embodiment, for training purposes, the display system 120 may display a virtual environment simulating a surgical site within a patient. The virtual environment may include various biological structures in addition to the surgical instrument 104. The surgeon 112 operates a virtual instrument within the virtual environment to train, obtain certification, or experiment with various skills or procedures without having the possibility of harming a real patient.

In either a live surgery or a simulated surgical procedure, the display system 120 may be used to present a user-interface to a user (e.g., the surgeon 112). In an embodiment, the display system 120 is a three-dimensional interface, such as a stereo display. In another embodiment, the display system 120 is used to project a three-dimensional image, such as from a high-definition endoscope camera. A user-interface may be displayed as an overlay, such as by using a translucent interface, or may be displayed in place of the view of the surgical field.

Figure 2A:
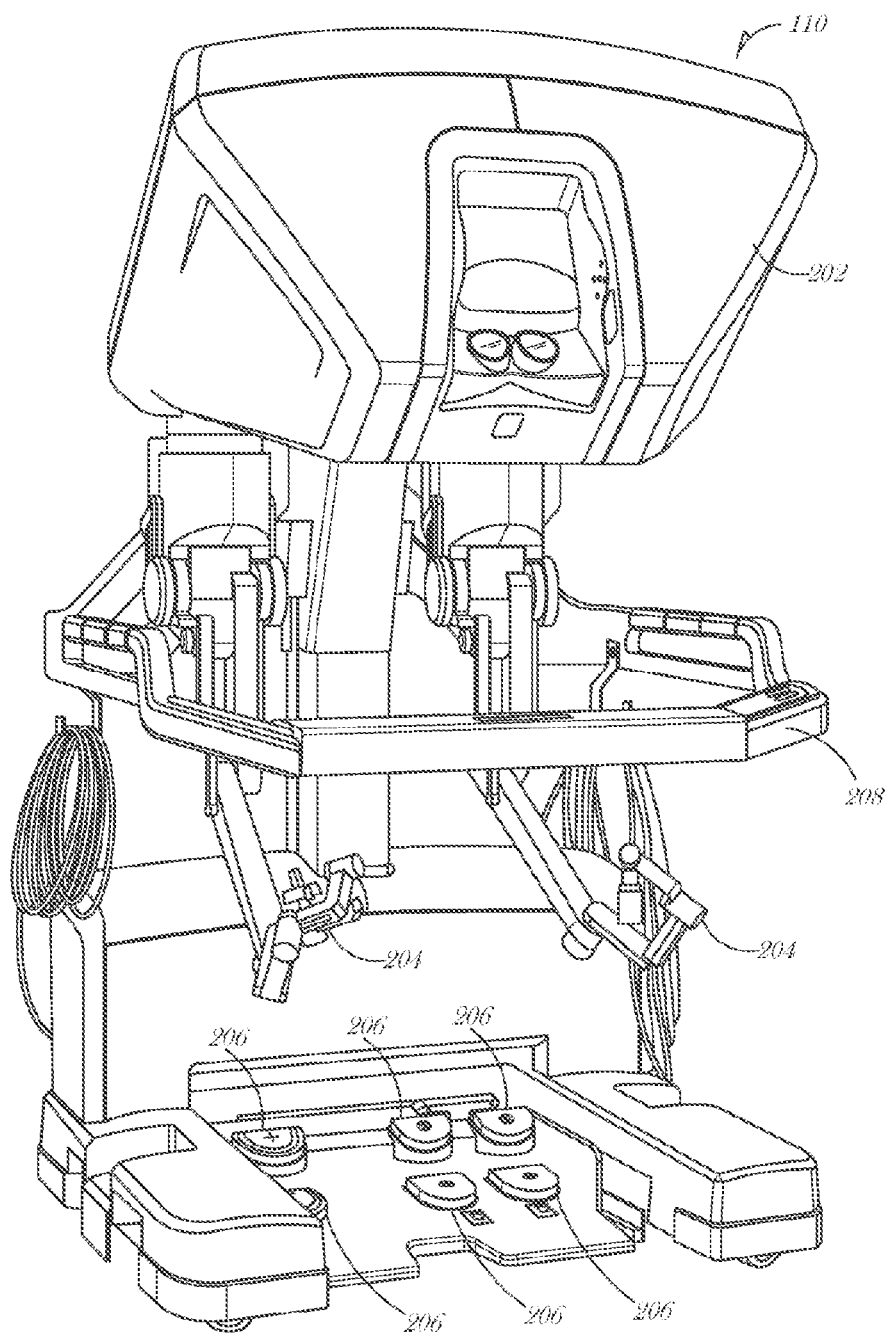
FIG. 2A is a drawing illustrating a master assembly, according to an embodiment.

FIG. 2A is a drawing illustrating a master assembly 110, according to an embodiment. A user may sit at the master assembly 110 and may access a display system 202, master controllers 204, and footswitch panel 206. The footswitch panel 206 enables the user to perform various tasks, such as swapping between various surgical instruments or controlling video or camera features. While seated at the master assembly 110, the user may rest their arms on an armrest 208. When operating in a live surgery, the display system 202 displays the surgical field as captured from a camera inserted through a small opening to the surgical site, sometimes referred to as a portal or a cannula. For training purposes, a simulated environment may be displayed on the display system 202, where the simulated environment may be a stereoscopic display of a surgical site and virtual slave surgical instruments. As the user moves the master controllers 204, a virtual surgical instrument may move in a corresponding fashion in the stereoscopic display.

Figure 2B:
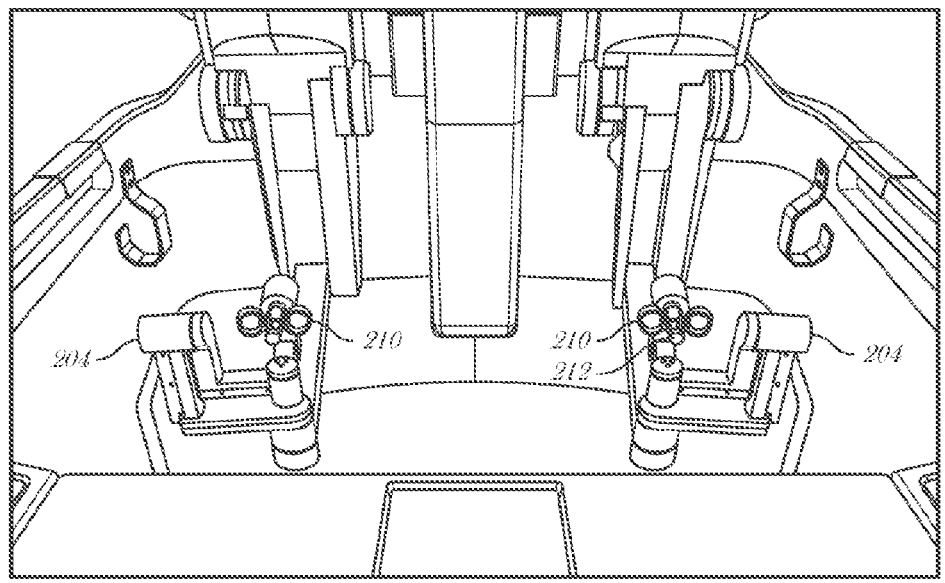
FIG. 2B is a drawing illustrating a master controller of a roaster assembly, according to an embodiment.

FIG. 2B is a drawing illustrating a master controller 204 of a master assembly 110, according to an embodiment. The master controller 204 includes a handheld part or gimbal. The master controller 204 has an articulated arm portion including a plurality of members or links connected together by pivotal connections or joints. The user grips finger loops 210 by positioning his or her thumb and index finger over a pincher formation 212. The user's thumb and index finger are typically held on the pincher formation by straps threaded through slots to create the finger loops 210. When the pincher formation 212 is squeezed between the thumb and index finger, the fingers or other element of the surgical instrument 104 move in synchronicity. The joints of the master controller 204 are operatively connected to actuators, e.g., electric motors, or the like, to provide for, e.g., force feedback, gravity compensation, and the like. Furthermore, appropriately positioned sensors, e.g., encoders, or potentiometers, or the like, are positioned on each joint of the master controller 204, so as to enable joint positions of the master controller 204 to be determined by the master assembly 110 or other control systems in the teleoperated surgical system 100.

In an embodiment, there are two master controllers 204, each with two finger loops 210 for which the user may insert an index finger and thumb of a respective hand. The two master controllers 204 may each control a virtual surgical instrument. The user may be provided software or hardware mechanisms to swap between multiple instruments for one or both master controller 204. For example, a user may be provided three instruments, such as two forceps and a retractor. One or both of the forceps may be an energy instrument able to cauterize tissue. The user may first use the forceps at each master controller 204, then switch the right master controller 204 to control the retractor to expose a section of the surgical field, and then switch the right master controller 204 hack to the forceps to continue cutting, probing, or dissecting tissue.

While using the master controllers 204, the user is provided with full three-dimensional range of motion (x, y, and z axis) along with rotational motion (roll, pitch, yaw) in addition to pinching motion with the index and thumb (or any two fingers inserted into the loops 210). As such, by moving the appropriate master controller 204, the user is able to manipulate the corresponding surgical instrument through a full range of motion.

Figure 2C:
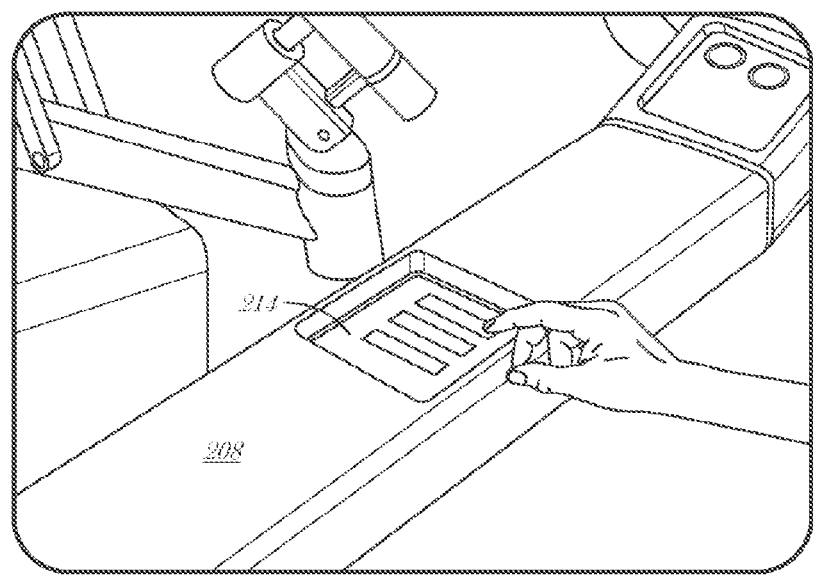
FIG. 2C is a drawing illustrating an armrest of a master assembly, according to an embodiment.

FIG. 2C is a drawing illustrating an armrest 208 of a master assembly 110, according to an embodiment. The armrest 208 may include one more touch controls, such as touchscreens, soft buttons, mechanical buttons, or the like. In the example illustrated in FIG. 2C, a single touchscreen 214 is shown through which the user may configure various video, audio, or other system settings.

Overview of User-Interface Control

During operation, the user may be presented a user interface at various times. For example, a user interface may be presented to allow the user to choose from a selection of training modules. As another example, a user interface may be presented to allow the user to configure various aspects of the operation of the master assembly 110. When the user has one or both hands operating a master controller 204, it may be inconvenient to have to release a master controller 204 and then operate another input mechanism, such as a touchscreen interface integrated into the armrest 208 of the master assembly 110.

Figure 3:
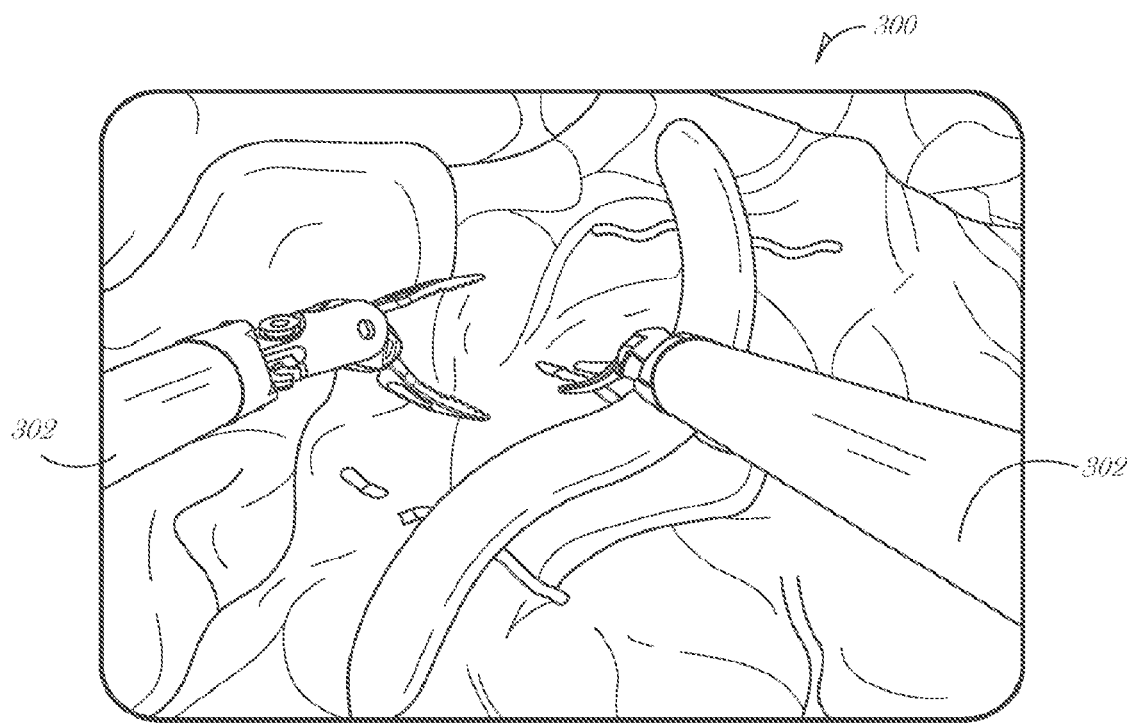
FIG. 3 illustrates a virtual surgical site according to an embodiment.

FIG. 3 illustrates a virtual surgical site according o an embodiment. The virtual surgical site 300 may be displayed on the display system 202 and includes two virtual slave surgical instruments 302. When operating in this mode, the master controller 204 is able to move in three-dimensions in free space (within the boundaries of the virtual surgical site 300). In a second mode, the master controller 204 is restricted to movement in a plane or on a surface. The second mode is used when a "flat" user interface is presented to the user. The second mode is useful to provide an operating space for the master controllers 204 that roughly matches the visual interface. In another embodiment, the user interface may be presented in a contoured user interface. A contoured user interface is a surface, which may include non-planar surfaces (e.g., curved surfaces).

Figure 4A:
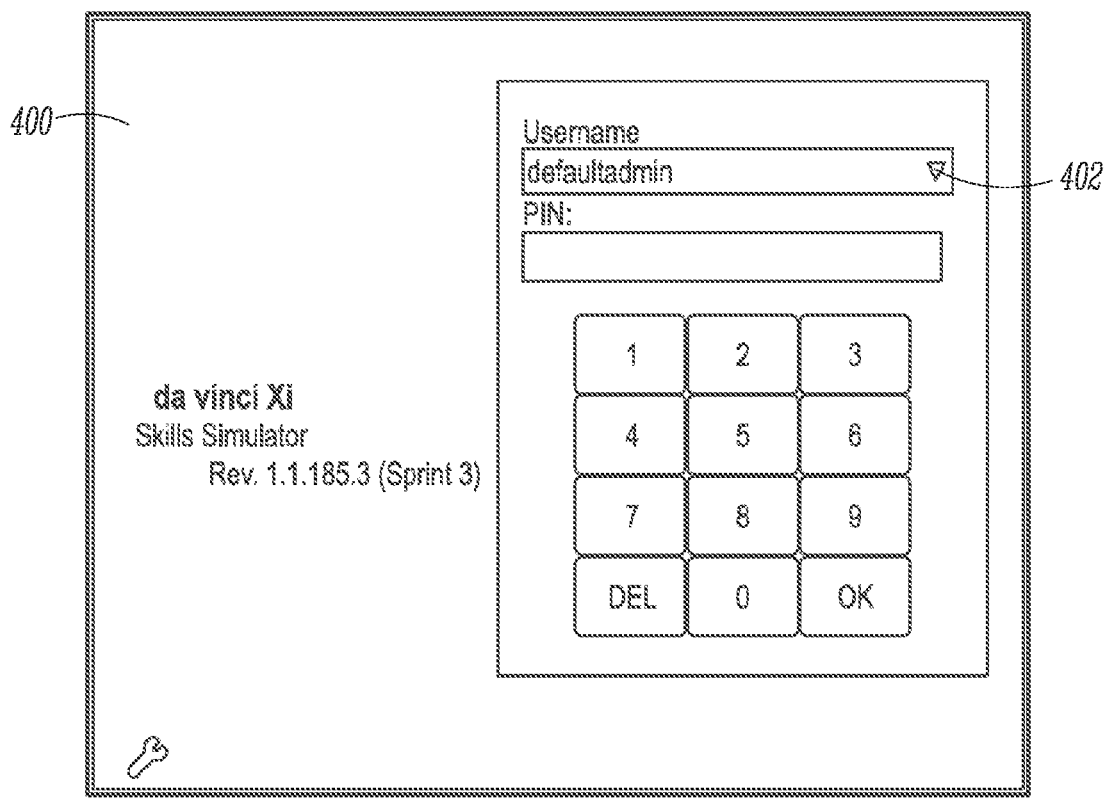
FIGS. 4A-4D illustrate user interfaces according to embodiments.
Figure 4B:
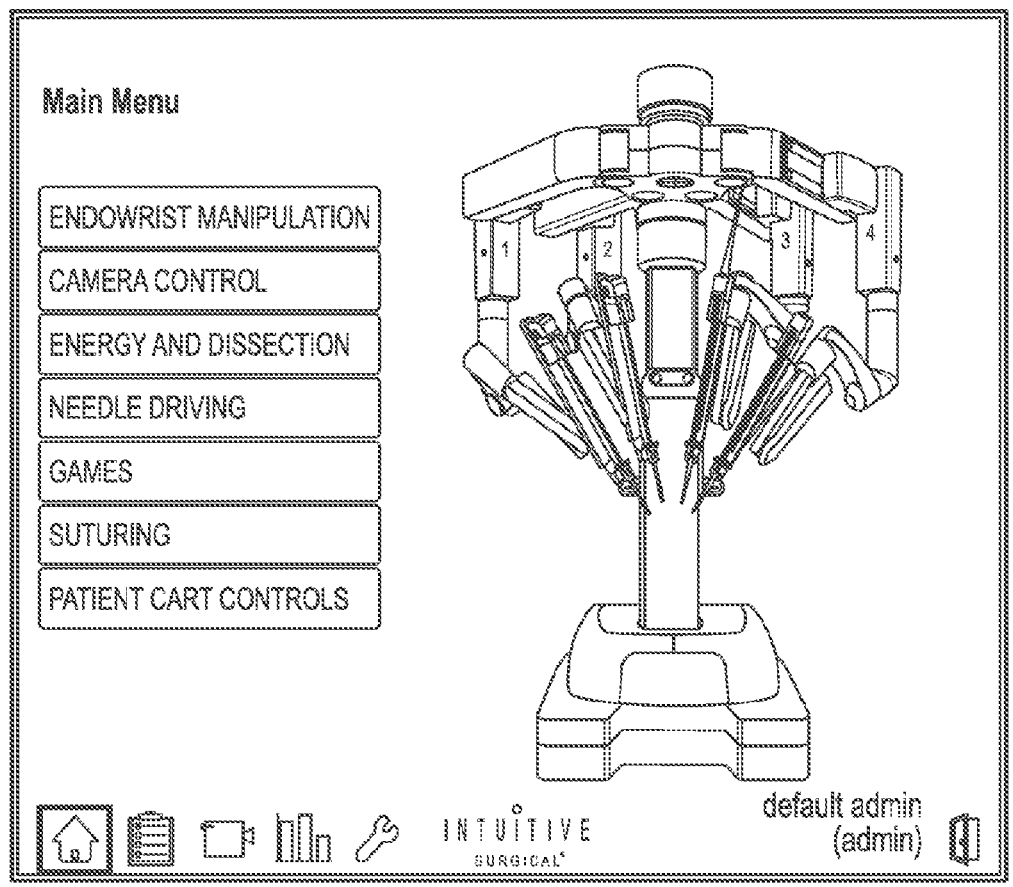
Figure 4C:
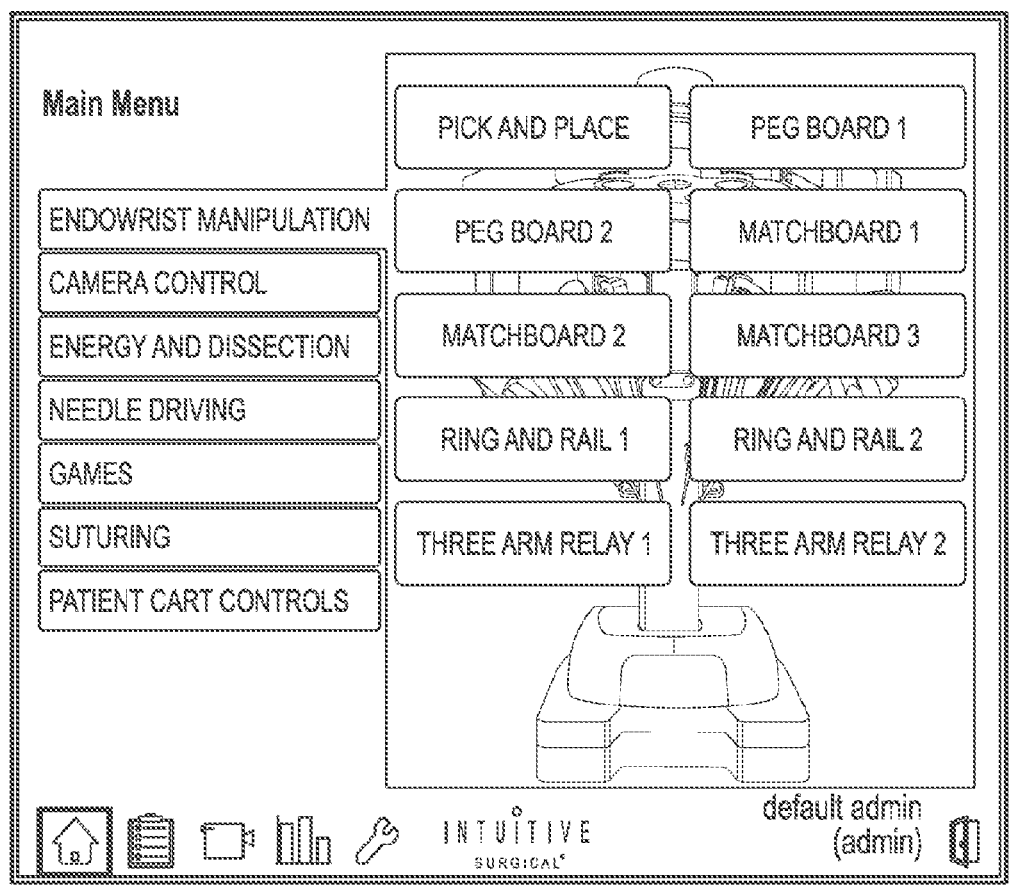
Figure 4D:
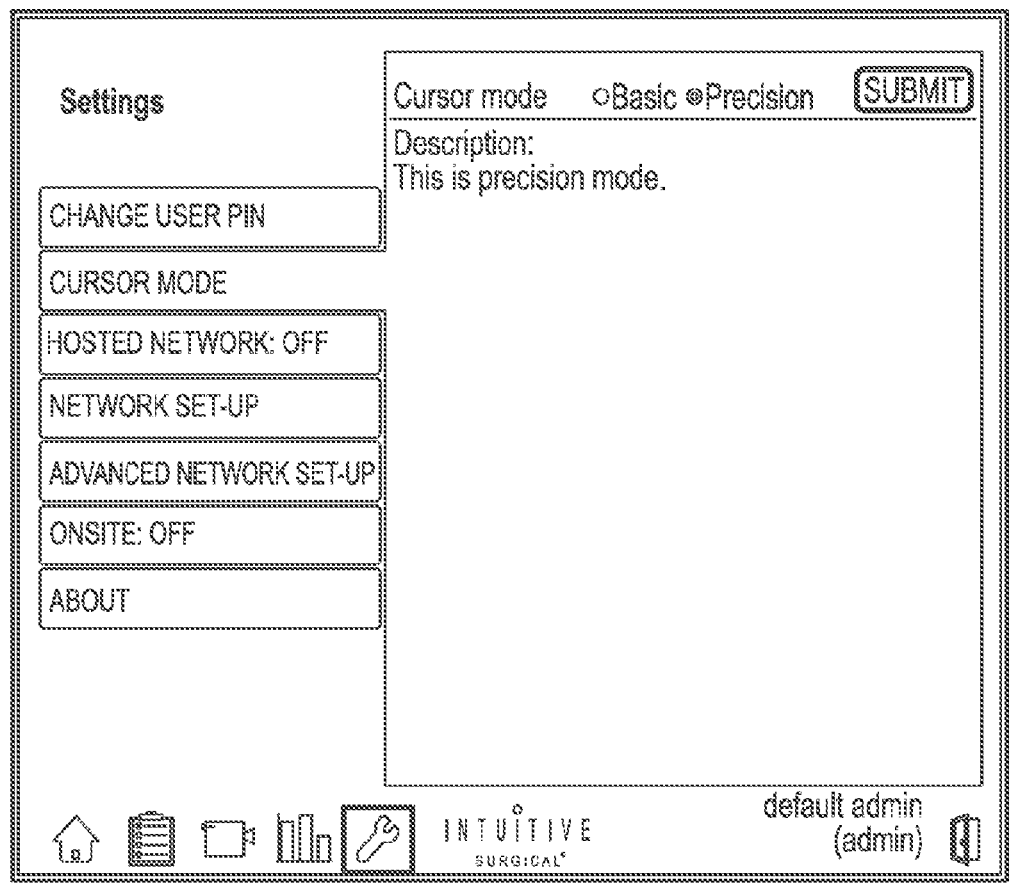
Figure 5:
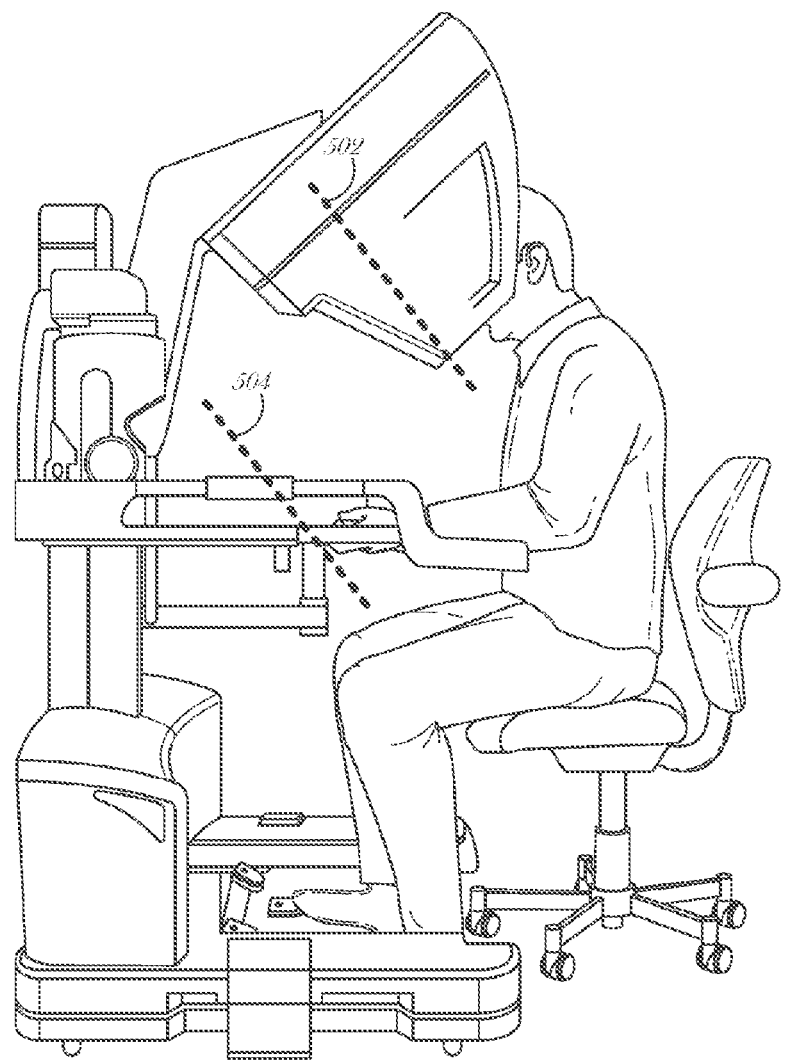
FIG. 5 is a diagram illustrating a viewing plane and a haptic plane, according to an embodiment.

FIG. 4A illustrates a user dace 400 according o an embodiment. The user interface 400 is optionally displayed as an overlay to the surgical site view or as a standalone interface. A pointer 402 is displayed within the user interface 400 and is used to activate one or more user interface controls, such as buttons, sliders, option lists, etc. The pointer 402 may be controlled by a master controller 204. Using the servo controls in the master controller 204, the user may be provided with haptic feedback to provide a sensation of touching a user interface control. For example, when the user presses a user interface button, slides a control, or moves a dial in the user interface, the master controller 204 may vibrate, shake, or otherwise react to the actuation of the user interface control to provide the user with sensory feedback. Where FIG. 4A illustrates a login screen, FIG. 4B illustrates a main menu screen, FIG. 4C illustrates an exercise selection screen, and FIG. 4D illustrates a settings screen. It is understood that more or fewer screens may be used in the user interface 400. The user interface 400 is presented as a flat interface (e.g., two-dimensional instead of three-dimensional). As such, when the user is controlling a pointer in the user interface, as opposed to controlling the virtual surgical instruments, the user may be constrained to a 2D plane. This may better simulate the planar dimensions of the user interface displayed to the user. If a 3D user interface is provided, then constraints on the movement of the input device (e.g., the master controller 204) may be removed or modified. Thus, when in the surgical simulation (e.g., a first mode), the user may have full or nearly full freedom of motion and after entering a configuration mode (e.g., a second mode) with a user interface displayed, the user may then be constrained to a plane. The constrained plane may be oriented in space such that the user's hands and master controllers 204 are at approximately the same angle as that displayed in the display system 202. Such correlation may assist the user to orient their hands in 3D space with respect to the user interface displayed. An example is illustrated in FIG. 5, which shows a viewing plane 502 and a haptic plane 504, The viewing plane 502 represents the user interface images perceived by the user in the display system 202. The haptic plane 504 is the plane that the master controllers 204 are constrained within. When a user attempts to move a master controller 204 "up" or "down" with respect to the a-axis of the haptic plane 504, the user may encounter resistance from such movement, Should the user change the orientation of the viewing plane 502, such as with a display configuration setting, then the haptic plane 504 may adjust to maintain an approximately parallel orientation with respect to the viewing plane 502. In various embodiments, the haptic plane may be oriented at a fixed or dynamic angle offset with respect to viewing plane. Alternatively, the haptic plane may be oriented with a fixed or dynamic angle offset with respect to the ground. A user may also alter the constraints, for example, the position or orientation of the haptic plane.

Other restrictions or constraints on movement of the input device (e.g., the master controller 204) can be implemented to assist the user while interacting with the user interface. For example, the master assembly 110 may assist the user when interacting with the user interface. As one example, the master assembly 110 or other portions of the teleoperated surgical system 100 may detect when a user is about to click a button or control in a user interface. After detecting that the user is about to click, the teleoperated surgical system 100 slows cursor movement to enhance precision. This may reduce or eliminate false clicks. Alternately, the intent of the user to click is detected in advance of the click actuation and the master controllers 204 is partially or completely locked to improve accuracy and precision of clicking or selecting a user interface element. Thus, either the cursor movement and/or the master controller 204 movements may be restricted or slowed. The intent to click is inferred from various changes in input, such as the position or movement of a pincher formation 212. As the user begins to close their fingers in the pincher formation 212 to effect a click in a user interface, the system cart restrict motion in the master assembly 110 or reduce or restrict pointer movement, which increases pointer accuracy and enhances user interface interaction. The pointer movement in a user interface may decrease as a function of speed or position of the pincher formation 212 closing. For example, the pincher formation 212 may move a total of 3 cm from a fully open position to a fully closed position. In a linear, exponential, or logarithmic manner, the speed of the pointer movement may decrease as a function of the amount the pincher formation 212 has closed. Thus, for example, when the pincher formation 212 achieves an open position of 1.5 cm, the speed of pointer movement may be decreased by 50% when using a linear function.

In another example, the user may "click" by pressing a foot pedal in the footswitch panel 206. The pedal position may be used to slow or stop a pointer or cursor's movement in the user interface, similar to the mechanics used with the master controllers 204.

In another example, the user may "click" a user interface element by pressing the master into the 2D plane. The user interface element, such as a button, may provide resistance to the user via the master controllers 204 to simulate a physical button press (e.g., resist to a point, then release).

In another example, the user's master controllers 204 may be moved to a default position in the user interface during an event. For example, when a user is provided a dialog box to accept or deny an action, the pointer may be moved to a default selection (e.g., accept) and the master controllers 204 may be moved to a corresponding position in their operating space. As another example, instead of moving the pointer directly to a user interface element, the user may be provided a suggestion by pushing the pointer (and master controllers 204) in the direction of a default user interface element. Similarly, the master controllers 204 can be controlled to resist movement away from a default user interface element. As such, when a user attempts to move the master controller 204 in a manner to move the pointer away from the user interface control, the master controller 204 provides haptic feedback, such as vibration or moderate resistance, the indicate to the user that the user interface has a suggested or recommended default user interface control.

In another example, the user may implement both master controllers 204 to simulate multi-touch or gestural input mechanisms. The master controllers 204 may be used to scroll, zoom, pan, rotate, or otherwise manipulate the view of the user interface. For example, the user may actuate both master controllers 204 by pinching the finger controls together on each master controller 204 and then move the master controllers 204 away from one another to zoom out. A similar motion may be used to zoom in, such as by actuating the master controllers 204 and moving them closer together. Panning and rotating may be implemented by actuating both controllers 204 and swiping left or right, or by moving them clockwise or counterclockwise around each other. Scrolling may be implemented by swiping in an upward or downward direction to move the view in the user interface up or down (this may be inverted based on user preference, such that by swiping upward, the view moves down and vice versa). One mode of scrolling simulates "grabbing" the thumb within a scrollbar to maneuver the viewable contents up or down in the view and the other mode of scrolling simulates "grabbing" the view and moving it up to see the contents that are lower on the user interface (and vice versa). Various content may be panned, scrolled, or otherwise positioned, such as windows, menus, dialog boxes, or other user interface elements.

Using the master controllers 204, a user may manipulate the position of a user interface overlay. For example, the user may change the position of a dialog box, menu system, modal box, or other user interface element by grabbing a title bar, using a particular gesture, or activating a particular user interface control (e.g., a button).

In another example, scrolling may be implemented by rotating the pincher formation 212 on a master controller 204. Zooming, panning, and other user interface controls may also be implemented using the rotating motion of the pincher formation 212.

When interacting with user interface controls, the master controllers 204 can provide haptic feedback to the user in order to simulate tactile user interface controls. For example, a slider user interface control may include notches such that when a slider thumb is moved into a notch, a slight vibration is applied to the master controller 204 to provide tactile feedback. As another example, when a button user interface control is pressed, the master controller 204 provides resistance to the user's action, until a breaking point, at which there is a release and the button is pressed. Such haptic feedback is used to better simulate physical properties of the user interface controls.

Figure 6:
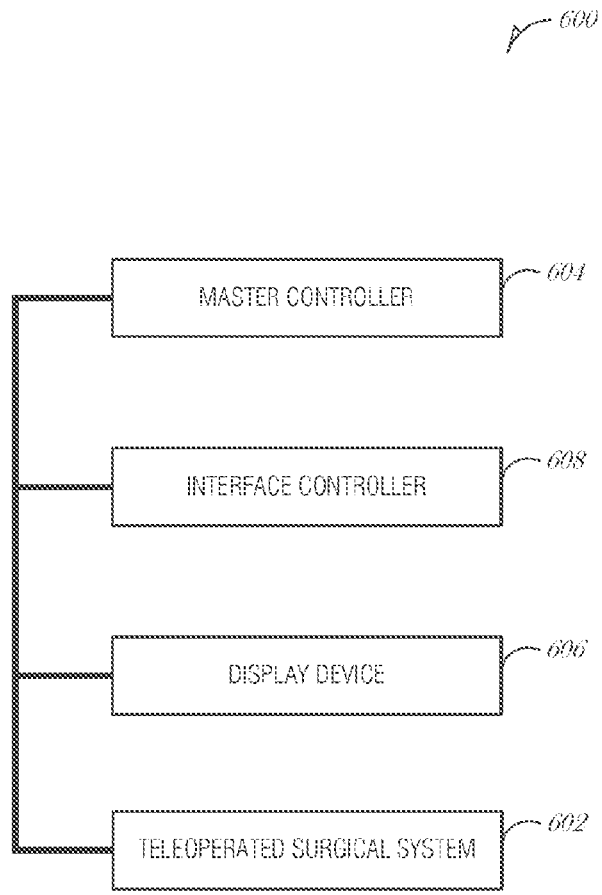
FIG. 6 is a block diagram illustrating a system to control a user interface of a teleoperated surgical system, according to an embodiment.

FIG. 6 is a block diagram illustrating a system 600 to control a user interface of a teleoperated surgical system 602, according to an embodiment. The system 600 includes a first master controller 604 communicatively coupled to the teleoperated surgical system 602.

The system 600 also includes a display device 606 communicatively coupled to the teleoperated surgical system and configured to display a graphical user interface. In an embodiment, the first master controller 604 is configured to transmit a first input signal to an interface controller 608, the first input signal caused by manual manipulation of the first master controller 604, the interface controller 608 to use the first input signal to update a graphical user interface presented by the display device 606.

In an embodiment, the interface controller 608 is configured to provide feedback to the first master controller 604 corresponding to the update of the graphical user interface.

In a further embodiment, to provide feedback, the interface controller 608 causes the first master controller 604 to vibrate. In a further embodiment, the interface controller 608 is configured to constrain the first master controller 604 to an operating space and cause the first master controller 604 to vibrate when the first master controller 604 encounters a boundary of the operating space. For example, the operating space may be the boundaries of a user interface presented on the display device 606, As another example, the operating space may be the boundaries of the visible area in the displayed environment.

In an embodiment, the graphical user interface comprises a user interface element, and vibrating the first master controller 604 is performed in conjunction with interaction with the user interface element. In an embodiment, the user interface element comprises a button, and vibrating the first master controller 604 is performed when the button is depressed. In an embodiment, the user interface element comprises a slider, and vibrating the first master controller 604 is performed when the slider is moved.

In an embodiment, the graphical user interface comprises a user interface element, where the user interface element comprises a button, and the feedback comprises using force feedback to provide resistance to the first master controller 604 when the button is depressed.

In an embodiment, the graphical user interface comprises a plurality of user interface elements where one of the plurality of user interface elements comprises a default user interface element, and the feedback comprises using force feedback to nudge the first master controller 604 toward a location corresponding to the default user interface element.

In an embodiment, the system 600 includes a second master controller communicatively coupled to the teleoperated surgical system 602 to transmit a second input signal to the interface controller 608, the second input signal caused by manual manipulation of the second master controller, the second input signal used by the interface controller 608 in conjunction with the first input signal to control the graphical user interface.

In an embodiment, the first input signal is caused by a rotating motion of the first master controller 604 and updating the graphical user interface comprises rotating a portion of the graphical user interface.

In an embodiment, to receive the first input signal from the first master controller 604, the interface controller 608 receives a rotational signal indicating that a portion of the first master controller 604 is manually rotated by an amount of rotation. In such an embodiment, updating the graphical user interface comprises scrolling a portion of the graphical user interface based on the amount of rotation.

In an embodiment, the first input signal is caused by a rotating motion of a portion of the first master controller 604, such as the pincher. In such an embodiment, updating the graphical user interface comprises rotating a portion of the graphical user interface. In a further embodiment, the rotating the portion of the graphical user interface is performed as a function of the rotating motion.

In an embodiment, the first input signal is caused by a manual pinching motion of a portion of the first master controller 604, and updating the graphical user interface comprises zooming a portion of the graphical user interface. In a further embodiment, the zooming is performed as a function of the pinching motion.

Figure 7:
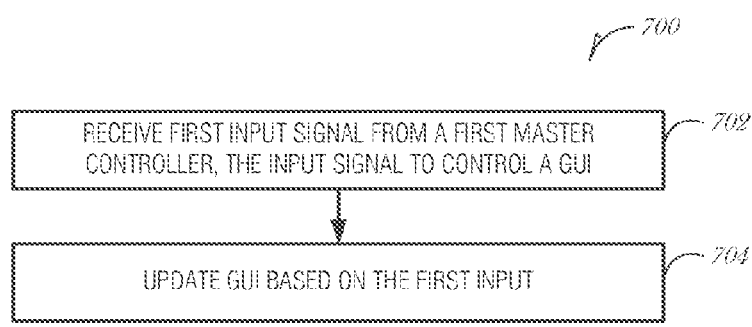
FIG. 7 is a flowchart illustrating a method of controlling a user interface, according to an embodiment.

FIG. 7 is a flowchart illustrating a method 700 of controlling a user interface, according to art embodiment. At block 702, a first input signal from a first master controller communicatively coupled to the teleoperated surgical system is received at a teleoperated surgical system, the first input signal to control an aspect of a graphical user interface presented by the teleoperated surgical system.

At block 704, the graphical user interface is updated based on the first input signal.

In a further embodiment, the method 700 comprises providing feedback to the first master controller corresponding to the graphical user interface. In an embodiment, providing feedback comprises vibrating the first master controller.

In an embodiment, the first master controller is constrained to an operating space and vibrating the first master controller is performed when the first master controller encounters a boundary of the operating space.

In an embodiment, the graphical user interface comprises a user interface element and vibrating the first master controller is performed in conjunction with interaction with the user interface element.

In an embodiment, the user interface element comprises a button, and vibrating the first master controller is performed when the button is depressed. In an embodiment, the user interface element comprises a slider, wherein vibrating the first master controller is performed when the slider is moved.

In an embodiment, the graphical user interface comprises a user interface element, where the user interface element comprises a button, and providing feedback comprises using force feedback to provide resistance to the first master controller when the button is depressed.

In an embodiment, the graphical user interface comprises a plurality of user interface elements where one of the plurality of user interface elements comprises a default user interface element, and providing feedback comprises using force feedback to nudge the master controller toward a location corresponding to the default user interface element.

In an embodiment, the method 700 includes receiving at the teleoperated surgical system, a second input signal from a second master controller communicatively coupled to the teleoperated surgical system, the second input signal to work in conjunction with the first input signal to control the aspect of the graphical user interface.

In an embodiment, the first input signal is caused by a rotating motion of the first master controller, and updating the graphical user interface comprises rotating a portion of the graphical user interface.

In an embodiment, receiving the first input signal from the first master controller comprises receiving a rotational signal indicating that a portion of the first master controller is rotated by an amount of rotation, and updating the graphical user interface comprises scrolling a portion of the graphical user interface based on the amount of rotation.

In an embodiment, the first input signal is caused by a rotating motion of a portion of the first master controller, and updating the graphical user interface comprises rotating a portion of the graphical user interface.

In an embodiment, the rotating the portion of the graphical user interface is performed as a function of the rotating motion.

In an embodiment, the first input signal is caused by a pinching motion of a portion of the first master controller; and updating the graphical user interface comprises zooming a portion of the graphical user interface. In a further embodiment, the zooming is performed as a function of the pinching motion.

Figure 8:
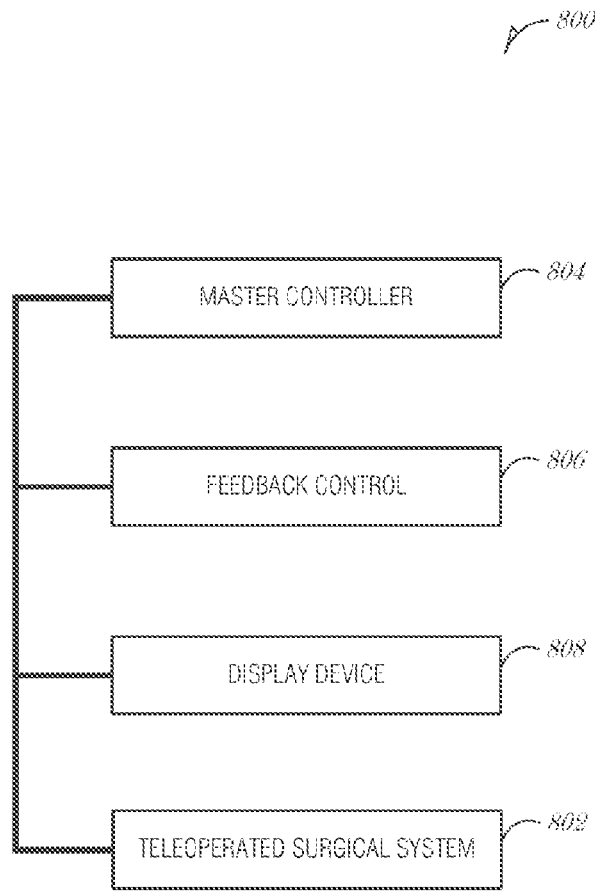
FIG. 8 is a block diagram illustrating a system to control the interaction between a user-interface of a teleoperated surgical system and a master controller 804 of the teleoperated surgical system, according to an embodiment.

FIG. 8 is a block diagram illustrating a system 800 to control the interaction between a user-interface of a teleoperated surgical system 802 and a master controller 804 of the teleoperated surgical system 802, according to an embodiment. The system 800 includes a first master controller 804 communicatively coupled to the teleoperated surgical system 802. The system 800 also includes a feedback control 806 communicatively coupled to the first master controller 804 and a display device 808 communicatively coupled to the teleoperated surgical system 802 and configured to display the user interface.

In an embodiment, the feedback control 806 is configured to constrain or restrict the movement of the first master controller 804 when the state of the user interface changes (i.e., when the interface provided by the user interface changes, such as from a 3D view of a surgical site or an anatomical model to a configuration screen or data entry form). In some embodiments, feedback control 806 can detect the change in state of the user interface and restrict movement of first master controller 804 in response. In various other embodiments, the restriction of motion of first master controller 804 can be initiated by the same action and/or instruction causing the change in state of the user interface (e.g., a user provides an input to change the user interface state that also initiates the motion restriction on first master controller 804).

In an embodiment, the state of the user interface is a two-dimensional user interface after having been transitioned from a previous state of a three-dimensional user interface, the two-dimensional user interface providing a viewing plane. In such an embodiment, to restrict the movement of the first master controller 804, the feedback control 806 is configured to restrict the first master controller 804 to a planar movement, thereby enforcing movement within a haptic plane. In some embodiments, the haptic plane can be oriented in space to approximate the viewing plane.

In an embodiment, the two-dimensional user interface comprises a contoured user interface, and wherein to restrict the movement of the first mater controller 804, the feedback control 806 is configured to restrict the first master controller 804 to a haptic shape corresponding to the contoured user interface. For example, if the user interface is presented as a concave bowl, the master controller 804 may follow the contour of the bowl shape in the operating space.

In an embodiment, the feedback control 806 is configured to detect that a pointer within the user interface and controlled by the movement of the first master controller 804 approaches an edge of the user interface and provide haptic feedback to the first master controller 804 in response to the pointer approaching the edge of the user interface. In a further embodiment, the haptic plane is bounded to approximate a viewing area of the viewing plane.

In an embodiment, the state of the user interface comprises a pointer in the user interface hovering over a clickable element of the user interface, and to restrict the movement of the first master controller, the feedback control 806 is configured to restrict movement of the first master controller 804 to decrease movement of the pointer while over the clickable element. In a further embodiment, to decrease movement comprises momentarily stopping the pointer while over the clickable element.

In an embodiment, the feedback control 806 is configured to, while the pointer is over the clickable element, determine that the first master controller is about to be actuated to produce a click.

In an embodiment, the first master controller 804 comprises a pincher formation and determining that the first master controller is about to be actuated to produce the click comprises detecting a change in position of the pincher formation. In a further embodiment, the pointer movement is decreased as a function of the change in position of the pincher formation.

In an embodiment, the first master controller 804 operates in three-dimensions in one mode and the state of the user interface is a two-dimensional user interface after having been transitioned from a previous state of a three-dimensional user interface, the two-dimensional user interface providing a viewing plane. In such an embodiment, to restrict the movement of the first master controller 804, the feedback control 806 is configured to restrict the first master controller 804 to a planar movement providing a haptic plane, the haptic plane oriented in space to approximate the viewing plane.

In an embodiment, to determine that the first master controller 804 is about to be actuated to produce the click, the feedback control 806 is configured to detect a change in position of the first master controller 804 orthogonal to the haptic plane. In a further embodiment, the pointer movement is decreased as a function of the change in position of the first master controller 804 with respect to the haptic plane.

In an embodiment, the state of the user interface comprises presenting a default user interlace control option in the user interface, and to restrict the movement of the first master controller 804, the feedback control 806 is configured to restrict movement of the first master controller 804 except in the direction of the default user interface control option.

In an embodiment, to restrict movement of the first master controller 804 except in the direction of the default user interface control option, the feedback control 806 is configured to provide haptic feedback to the first master controller 804 to nudge the first master controller to a position in space corresponding to the default user interface control option.

In an embodiment, to restrict movement of the first master controller 804 except in the direction of the default user interface control option, the feedback control 806 is configured to provide haptic feedback to resist movement of the first master controller to move the first master controller away from the position of the default user interface control option.

In an embodiment, the first master controller 804 operates in three-dimensions in one mode, and the state of the user interface is a two-dimensional user interface after having been transitioned from a previous state of a three-dimensional user interface, the two-dimensional user interface providing a viewing plane. In such an embodiment, to restrict the movement of the first master controller 804, the feedback control 806 is configured to restrict the first master controller 804 to a planar movement providing a haptic plane, the haptic plane oriented in space to approximate the viewing plane.

Figure 9:
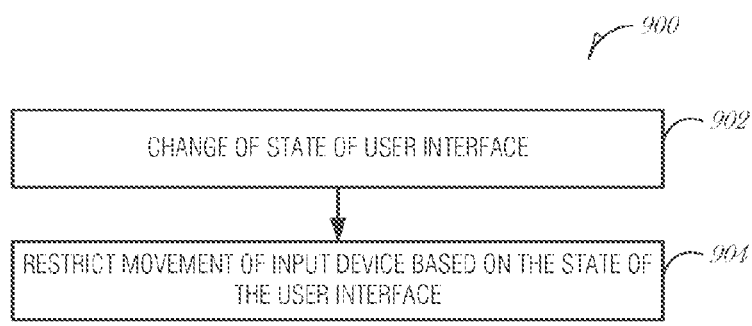
FIG. 9 is a flowchart illustrating a method of controlling the interaction between a user-interface of a teleoperated surgical system and an input device of the teleoperated surgical system, according to an embodiment.

FIG. 9 is a flowchart illustrating a method 900 of controlling the interaction between a user-interface of a teleoperated surgical system and an input device of the teleoperated surgical system, according to an embodiment. At block 902, a state of the user interface of the teleoperated surgical system changes.

At block 904, the movement of the input device is restricted (or becomes less restricted) based on the new state of the user interface. In an embodiment, the input device comprises a master controller.

In an embodiment, the state of the user interface is a two-dimensional user interface after having been transitioned from a previous state of a three-dimensional user interface, the two-dimensional user interface providing a viewing plane; and restricting the movement of the input device comprises restricting the input device to a planar movement providing a haptic plane, the haptic plane oriented in space to approximate the viewing plane.

In an embodiment, the two-dimensional user interface comprises a contoured user interface, and wherein restricting the movement of the input device comprises restricting the input device to a haptic shape corresponding to the contoured user interface.

In an embodiment, the method 900 includes detecting that a pointer within the user interface and controlled by the movement of the input device approaches an edge of the user interface; and providing haptic feedback to the input device in response to the pointer approaching the edge of the user interface. In an embodiment, the haptic plane is bounded to approximate a viewing area of the viewing plane.

In an embodiment, the state of the user interface comprises a pointer in the user interface hovering over a clickable element of the user interface; and restricting the movement of the input device comprises restricting movement of the input device to decrease movement of the pointer while over the clickable element. In a further embodiment, to decrease movement comprises momentarily stopping the pointer while over the clickable element.

In a further embodiment, while the pointer is over the clickable element, determining that the input device is about to be actuated to produce a click. In an embodiment, the input device comprises a pincher formation; and determining that the input device is about to be actuated to produce the click comprises detecting a change in position of the pincher formation. In an embodiment, the pointer movement is decreased as a function of the change in position of the pincher formation.

In an embodiment, the input device operates in three-dimensions in one mode; and the state of the user interface is a two-dimensional user interface after having been transitioned from a previous state of a three-dimensional user interface, the two-dimensional user interface providing a viewing plane; and restricting the movement of the input device comprises restricting the input device to a planar movement providing a haptic plane, the haptic plane oriented in space to approximate the viewing plane.

In an embodiment, determining that the input device is about to be actuated to produce the click comprises detecting a change in position of the input device orthogonal to the haptic plane. In a further embodiment, the pointer movement is decreased as a function of the change in position of the input device with respect to the haptic plane.

In an embodiment, the state of the user interface comprises presenting a default user interface control option in the user interface; and restricting the movement of the input device comprises restricting movement of the input device except in the direction of the default user interface control option. In a further embodiment, restricting movement of the input device except in the direction of the default user interface control option comprises: providing haptic feedback to the input device to nudge the input device to a position in space corresponding to the default user interface control option.

In an embodiment, restricting movement of the input device except in the direction of the default user interface control option comprises: providing haptic feedback to resist movement of the input device to move the input device away from the position of the default user interface control option.

In an embodiment, the input device operates in three-dimensions in one mode; and the state of the user interface is a two-dimensional user interface after having been transitioned from a previous state of a three-dimensional user interface, the two-dimensional user interface providing a viewing plane; and wherein restricting the movement of the input device comprises restricting the input device to a planar movement providing a haptic plane, the haptic plane oriented in space to approximate the viewing plane.

Computer Hardware and Storage Devices

Figure 10:
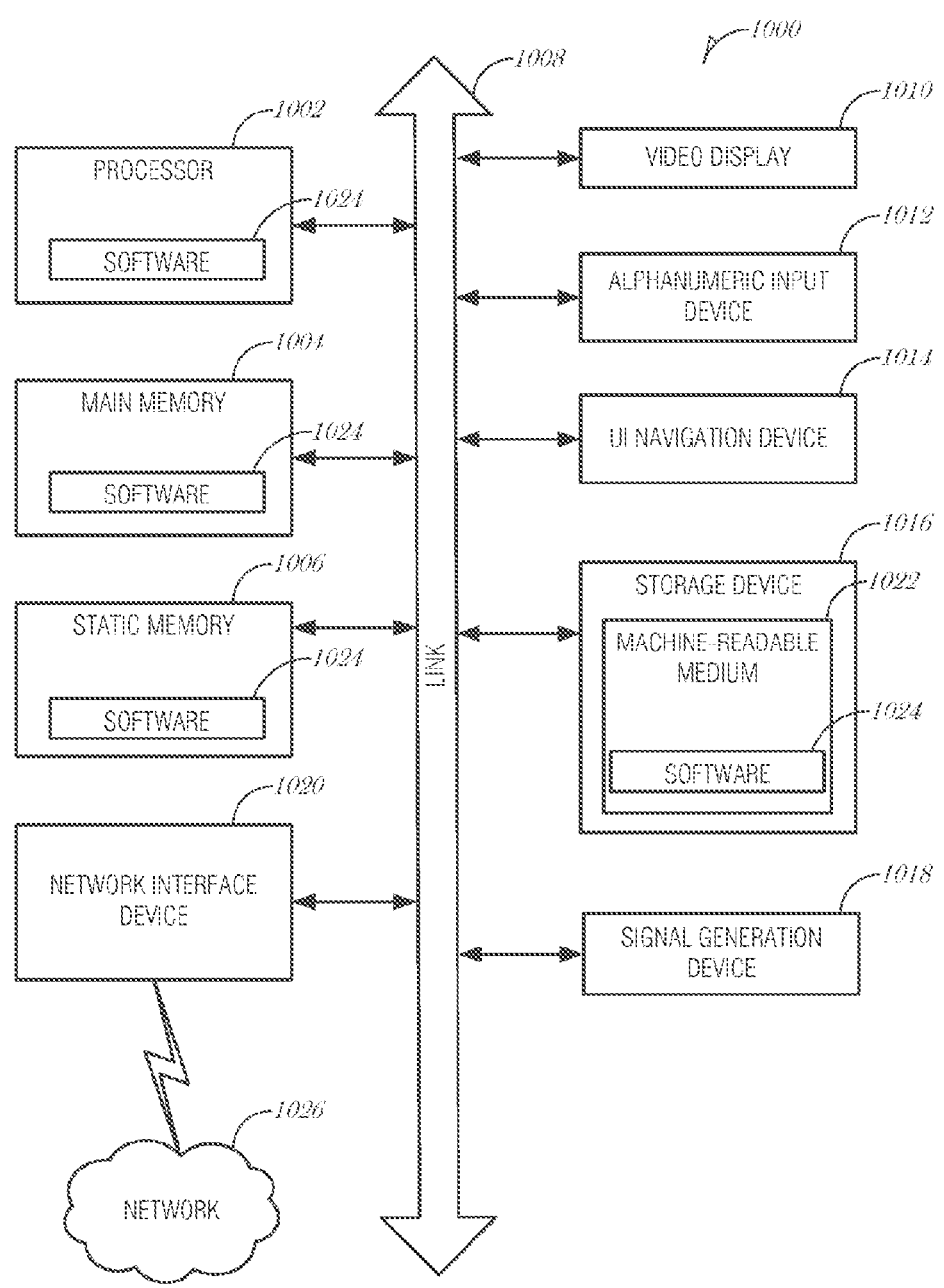
FIG. 10 is a block diagram illustrating an example machine upon which any one or more of the techniques (e.g., methodologies) discussed herein may perform, according to an example embodiment.

FIG. 10 is a block diagram illustrating an example machine upon which any one or more of the techniques (e.g., methodologies) discussed herein may perform, according to an example embodiment. FIG. 10 shows an illustrative diagrammatic representation of a more particularized computer system 1000. The computer system 1000 can be configured to implement, for example, a computerized training module. In alternative embodiments, the computer system 1000 operates as a standalone device or may be connected (e.g., networked) to other machines. In a networked deployment, the computer system 1000 may operate in the capacity of a server or a client machine in server-client network environment, or as a peer machine in a peer-to-peer (or distributed) network environment. The computer system 1000 may be a server computer, a client computer, a personal computer (PC), a tablet PC, a Personal Digital Assistant (PDA), a cellular telephone, or any machine capable of executing a set of instructions (sequential or otherwise) that specify actions to be taken by that machine. Further, while only a single machine (i.e., computer system 1000) is illustrated, the term "machine" shall also be taken to include any collection of machines that individually or jointly execute a set (or multiple sets) of instructions to perform any one or more of the methodologies discussed herein.

The example computer system 1000 includes a processor 1002 (e.g., a central processing unit (CPU), a graphics processing unit (GPU), or both), a main memory 1004 and a static memory 1006, which communicate with each other via a bus 1008. The computer system 1000 may further include a video display unit 1010 (e.g., liquid crystal display (LCD), organic light emitting diode (OLED) display, touch screen, or a cathode ray tube (CRT)) that can be used to display positions of the surgical instrument 104, for example. The computer system 1000 also includes an alpha-numeric input device 1012 (e.g., a keyboard, a physical keyboard, a virtual keyboard using software), a cursor control device or input sensor 1014 (e.g., a mouse, a track pad, a trackball, a sensor or reader, a machine readable information reader, bar code reader), a disk drive unit 1016, a signal generation device 1018 (e.g., a speaker) and a network interface device or transceiver 1020.

The disk drive unit 1016 includes a non-transitory machine-readable storage device medium 1022 on which is stored one or more sets of instructions 1024 (e.g., software) embodying any one or more of the methodologies or functions described herein. The instructions 1024 may also reside, completely or at least partially-, within the main memory 1004, static memory 1006 and/or within the processor 1002 during execution thereof by the computer system 1000, the main memory 1004 and the processor 1002 also constituting non-transitory machine-readable storage device media. The non-transitory machine-readable storage device medium 1022 also can store an integrated circuit design and waveform structures. The instructions 1024 may further be transmitted or received over a network 1026 via the network interface device or transceiver 1020.

While the machine-readable storage device medium 1022 is shown in an example embodiment to be a single medium, the term "machine-readable medium," "computer readable medium," and the like should be taken to include a single medium or multiple media (e.g., a centralized or distributed database, and/or associated caches and servers) that store the one or more sets of instructions 1024. The term "machine-readable medium" shall also be taken to include any medium that is capable of storing, encoding or carrying a set of instructions for execution by the machine and that cause the machine to perform any one or more of the methodologies of the present disclosure. The term "machine-readable medium" shall accordingly be taken to include, but not be limited to, solid-state memories, optical and magnetic media, and carrier wave signals.

It will be appreciated that, for clarity purposes, the above description may describe some embodiments with reference to different functional units or processors. However, it will be apparent that any suitable distribution of functionality between different functional units, processors or domains may be used without detracting from the present disclosure. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Although the present disclosure has been described in connection with some embodiments, it is not intended to be limited to the specific form set forth herein. One skilled in the art would recognize that various features of the described embodiments may be combined in accordance with the present disclosure. Moreover, it will be appreciated that various modifications and alterations may be made by those skilled in the art without departing from the spirit and scope of the present disclosure.

In addition, in the foregoing detailed description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the detailed description, with each claim standing on its own as a separate embodiment.

The foregoing description and drawings of embodiments in accordance with the present invention are merely illustrative of the principles of the inventive subject matter. Therefore, it will be understood that various modifications can be made to the embodiments by those skilled in the art without departing from the spirit and scope of the inventive subject matter, which is defined in the appended claims.

Thus, while certain exemplary embodiments of the invention have been described and shown in the accompanying drawings, it is to be understood that such embodiments are merely illustrative of and not restrictive on the broad inventive subject matter, and that the embodiments of the invention not be limited to the specific constructions and arrangements shown and described, since various other modifications may occur to those ordinarily skilled in the art.

What is claimed is:

1. A method of interactive control of a teleoperated surgical system, the method comprising:
   displaying at the teleoperated surgical system, a two-dimensional graphical user interface, wherein the two-dimensional graphical user interface includes (i) a graphical pointer that is moveable in two dimensions within the two-dimensional graphical user interface, (ii) a clickable element configured to be interacted with using the graphical pointer, and (iii) a user viewing plane;
   constraining movement of a first master controller from a three-dimensional haptic space to a two-dimensional haptic plane oriented based on the user viewing plane of the two-dimensional graphical user interface;
   receiving, at the teleoperated surgical system, sensor input indicating the two-dimensional movement of the first master controller constrained to the two-dimensional haptic plane, the sensor input to control movement of the graphical pointer, to move the graphical pointer within the two-dimensional graphical user interface correspondingly with the movement of the first master controller within the two-dimensional haptic plane;
   in response to detecting a user intent to interact with the clickable element using the graphical pointer, further constraining the movement of the first master controller within the two-dimensional haptic plane to affect the movement of the graphical pointer within the two-dimensional graphical user interface; and
   detecting the user intent to interact with the clickable element using the graphical pointer based upon a change in speed of closing of a pincher formation of the first master controller.

2. The method of claim 1, further including:
   detecting the user intent to interact with the clickable element based upon a position of the graphical pointer in relation to the clickable element in the two-dimensional graphical user interface.

3. The method of claim 1,
   wherein further constraining the movement of the first master controller within the two-dimensional haptic plane to affect the movement of the graphical pointer within the two-dimensional graphical user interface includes constraining the movement of the first master controller in the two-dimensional haptic plane to reduce the corresponding movement of the graphical pointer within the two-dimensional graphical user interface.

4. The method of claim 1, further including:
   wherein further constraining the movement of the first master controller within the two-dimensional haptic plane to affect the movement of the graphical pointer within the two-dimensional graphical user interface includes at least partially locking the first master controller to stop the corresponding movement of the graphical pointer within the two-dimensional graphical user interface.

5. The method of claim 1, further including:
   detecting the user intent to interact with the clickable element in response to the graphical pointer hovering over the clickable element in the two-dimensional graphical user interface;
   further constraining the movement of the first master controller within the two-dimensional haptic plane to affect the movement of the graphical pointer within the two-dimensional graphical user interface while the graphical pointer hovers over the clickable element.

6. The method of claim 1, further including:
   detecting the user intent to interact with the clickable element based upon an amount that the pincher formation of the first master controller is closed.

7. The method of claim 6, further including:
wherein further constraining the movement of the first master controller within the two-dimensional haptic plane to affect the movement of the graphical pointer includes slowing the movement of the graphical pointer as a function of change in the amount that the pincher formation of the first master controller is closed.

8. The method of claim 6, further including:
wherein further constraining the movement of the first master controller within the two-dimensional haptic plane to affect the movement of the graphical pointer includes limiting the movement of the graphical pointer as a function of change in the amount that the pincher formation of the first master controller is closed.

9. The method of claim 8,
wherein further constraining the movement of the first master controller within the two-dimensional haptic plane to affect the movement of the graphical pointer includes decreasing the movement of the graphical pointer as the function of change in the amount that the pincher formation of the first master controller is closed in at least one of a linear, exponential, or logarithmic manner.

10. The method of claim 1,
wherein further constraining the movement of the first master controller within the two-dimensional haptic plane to affect the movement of the graphical pointer includes slowing the movement of the graphical pointer as a function of the change in speed of closing of the pincher formation of the first master controller.

11. The method of claim 1,
wherein further constraining the movement of the first master controller within the two-dimensional haptic plane to affect the movement of the graphical pointer includes limiting the movement of the graphical pointer as a function of the change in speed of closing of the pincher formation of the first master controller.

12. A control system to interactively control a teleoperated surgical system, the control system comprising:
a first master controller communicatively coupled to the teleoperated surgical system;
a display device communicatively coupled to the teleoperated surgical system;
wherein the control system is configured to:
display at the display device a two-dimensional graphical user interface, wherein the two-dimensional graphical user interface includes (i) a graphical pointer that is moveable in two dimensions within the two-dimensional graphical user interface, (ii) a clickable element configured to be interacted with using the graphical pointer, and (iii) a user viewing plane;
constrain movement of the first master controller from a three-dimensional haptic space to a two-dimensional haptic plane oriented based on the user viewing plane of the two-dimensional graphical user interface;
receive sensor input indicating the two-dimensional movement of the first master controller constrained to the two-dimensional haptic plane, the sensor input to control movement of the graphical pointer, to move the graphical pointer within the two-dimensional graphical user interface correspondingly with the movement of the first master controller within the two-dimensional haptic plane;
in response to detecting a user intent to interact with the clickable element using the graphical pointer, further constrain the movement of the first master controller within the two-dimensional haptic plane to affect the movement of the graphical pointer within the two-dimensional graphical user interface; and
detect the user intent to interact with the clickable element using the graphical pointer based upon a change in speed of closing of a pincher formation of the first master controller.

13. The control system of claim 12, wherein the control system is further configured to,
detect the user intent to interact with the clickable element based upon a position of the graphical pointer in relation to the clickable element in the two-dimensional graphical user interface.

14. The control system of claim 12,
wherein further constraining the movement of the first master controller within the two-dimensional haptic plane to affect the movement of the graphical pointer within the two-dimensional graphical user interface includes constraining the movement of the first master controller in the two-dimensional haptic plane to reduce the corresponding movement of the graphical pointer within the two-dimensional graphical user interface.

15. The control system of claim 12,
wherein further constraining the movement of the first master controller within the two-dimensional haptic plane to affect the movement of the graphical pointer within the two-dimensional graphical user interface includes at least partially locking the first master controller to stop the corresponding movement of the graphical pointer within the two-dimensional graphical user interface.

16. The control system of claim 12, wherein the control system is further configured to,
detect the user intent to interact with the clickable element in response to the graphical pointer hovering over the clickable element in the two-dimensional graphical user interface;
further constraining the movement of the first master controller within the two-dimensional haptic plane to affect the movement of the graphical pointer within the two-dimensional graphical user interface while the graphical pointer hovers over the clickable element.

17. The control system of claim 12, wherein the control system is further configured to,
detect the user intent to interact with the clickable element based upon an amount that the pincher formation of the first master controller is closed.

18. The control system of claim 17,
wherein further constraining the movement of the first master controller within the two-dimensional haptic plane to affect the movement of the graphical pointer includes slowing the movement of the graphical pointer as a function of change in the amount that the pincher formation of the first master controller is closed.

19. The control system of claim 17,
wherein further constraining the movement of the first master controller within the two-dimensional haptic plane to affect the movement of the graphical pointer includes limiting the movement of the graphical pointer as a function of change in the amount that the pincher formation of the first master controller is closed.

20. The control system of claim 19,
Wherein further constraining the movement of the first master controller within the two-dimensional haptic plane to affect the movement of the graphical pointer includes decreasing the movement of the graphical pointer as the function of change in the amount that the pincher formation of the first master controller is closed in at least one of a linear, exponential, or logarithmic manner.

21. The control system of claim 12, wherein further constraining the movement of the first master controller within the two-dimensional haptic plane to affect the movement of the graphical pointer includes slowing the movement of the graphical pointer as a function of the change in speed of closing of the pincher formation of the first master controller.

22. The control system of claim 12, wherein further constraining the movement of the first master controller within the two-dimensional haptic plane to affect the movement of the graphical pointer includes limiting the movement of the graphical pointer as a function of the change in speed of closing of the pincher formation of the first master controller is.

* * * * *

UNITED STATES PATENT AND TRADEMARK OFFICE
CERTIFICATE OF CORRECTION

PATENT NO. : 12,336,773 B2  
APPLICATION NO. : 17/016340  
DATED : June 24, 2025  
INVENTOR(S) : Suresh et al.

Page 1 of 1

It is certified that error appears in the above-identified patent and that said Letters Patent is hereby corrected as shown below:

On the Title Page

In Column 2, under item (56) "Other Publications", Line 1, delete "eat" and insert --et-- therefor In the Claims In Column 18, Line 63, in Claim 20, delete "Wherein" and insert --wherein-- therefor In Column 19, Line 17, in Claim 22, delete "controller is." and insert --controller.-- therefor Signed and Sealed this  
Twenty-second Day of July, 2025

Coke Morgan Stewart  
*Acting Director of the United States Patent and Trademark Office*